United States Patent [19]

Hudson et al.

[11] 4,191,741
[45] Mar. 4, 1980

[54] REMOVABLE DRUG IMPLANT

[75] Inventors: James L. Hudson, Indianapolis; Jack F. Wagner, Greenfield, both of Ind.

[73] Assignee: Eli Lilly and Company, Indianapolis, Ind.

[21] Appl. No.: 944,946

[22] Filed: Sep. 22, 1978

[51] Int. Cl.² .................. A61M 7/00; A61K 27/12; A61K 9/00; A61K 9/52
[52] U.S. Cl. .................... 424/19; 128/260; 424/28; 424/78
[58] Field of Search .................... 424/19–22, 424/28, 78; 128/260

[56] References Cited

U.S. PATENT DOCUMENTS

| Re. 28,536 | 9/1975 | Reed | 128/264 |
|---|---|---|---|
| 3,279,996 | 10/1966 | Long et al. | 424/32 |
| 3,499,445 | 3/1970 | Reed | 128/260 |
| 3,545,439 | 12/1970 | Duncan | 128/260 |
| 3,920,805 | 11/1975 | Roseman | 424/15 |
| 3,946,106 | 3/1976 | Chien et al. | 424/15 |
| 3,992,518 | 11/1976 | Chien et al. | 424/22 |
| 4,012,496 | 3/1977 | Schopflin | 424/15 |
| 4,012,497 | 3/1977 | Schopflin | 424/22 |
| 4,053,580 | 10/1977 | Chien et al. | 424/15 |
| 4,096,239 | 6/1978 | Katz et al. | 424/21 |

OTHER PUBLICATIONS

Cooney, AI ChE Journal, May 1971, pp. 754–756, Slow Dissolution of Implanted Beds of Spherical Particles as a Method for Prolonged Release Medication, ("Medicine Compounded on an Inert Core").

Primary Examiner—Shep K. Rose
Attorney, Agent, or Firm—Leroy Whitaker; Arthur R. Whale

[57] ABSTRACT

There is disclosed an implant which has an inert, biocompatible core with a coating comprising from about 5 to about 40% of estradiol in a biocompatible dimethylpolysiloxane rubber. When the implant is placed under the skin of a ruminant animal the estradiol is released at a substantially constant rate to produce a greater than normal weight gain in the animal. The implant remains intact and may be removed from the animal at the end of the desired period of drug administration.

7 Claims, No Drawings

REMOVABLE DRUG IMPLANT

BACKGROUND OF THE INVENTION

This invention pertains to animal drug delivery systems. More particularly this invention pertains to a non-degradable implant for the administration of a substantially constant rate of estradiol to a ruminant animal, which implant may be removed from the animal at the end of the drug administration period.

Long et al. U.S. Pat. No. 3,279,996 describes an implant for releasing a drug in the tissues of a living organism comprising the drug enclosed in a capsule formed of silicone rubber. The drug migrates through the silicone rubber wall and is slowly released into the living tissues. A number of biocompatible silicone rubbers are described in the Long et al. patent. When a drug delivery system such as that described in U.S. Pat. No. 3,279,996 is used in an effort to administer estradiol to a ruminant animal a number of problems are encountered. For example, an excess of the drug is generally required in the hollow cavity of the implant. Also, it is difficult to achieve a constant rate of administration of the drug over a long time period such as from 200 to 400 days as would be necessary for the daily administration of estradiol to a growing beef animal.

Katz et al. U.S. Pat. No. 4,096,239 describes an implant pellet containing estradiol or estradiol benzoate which has an inert spherical core and a uniform coating comprising a carrier and the drug. The coating containing the drug must be both biocompatible and biosoluble, i.e., the coating must dissolve in the body fluids which act upon the pellet when it is implanted in the body. The rate at which the coating dissolves determines the rate at which the drug is released. Representative carriers for use in the coating material include cholesterol, solid polyethylene glycols, high molecular weight fatty acids and alcohols, biosoluble waxes, cellulose derivatives and solid polyvinyl pyrrolidone. A silicone rubber cannot be used in the coating of the implant of U.S. Pat. 4,096,239 since the silicone rubber does not dissolve in body fluids.

SUMMARY OF THE INVENTION

We have now discovered an implant for the administration of estradiol to a ruminant animal at a substantially constant rate which comprises a core of an inert, biocompatible material coated with a dimethylpolysiloxane rubber containing from 5% to 40% estradiol. A preferred form of the implant is a cylinder of from about 0.5 to about 6 cm. in length containing an inert, biocompatible core of about 2 to about 10 mm. in diameter with an estradiolcontaining coating of dimethylpolysiloxane of about 0.2 to about 1 mm. thickness. The inert core material may be exposed at the ends of the cylinder or may be covered with the drug-containing coating.

This invention also comprises a process for the administration of estradiol to a ruminant animal, especially a steer, to improve the rate of weight gain of the animal by placing the implant of this invention under the skin of the animal. The implant may be removed from the animal prior to slaughter.

DESCRIPTION OF THE PREFERRED EMBODIMENT

Estradiol is a naturally occurring estrogen which can be administered to ruminant animals to improve the rate of gain of the animals. For optimum results the estradiol should be administered at a substantially constant daily rate. It is an object of this invention to provide a means for such administration.

When an implant of the present invention is placed under the skin of a ruminant animal, such as a growing beef animal, an effective amount of estradiol is released from the implant at a substantially constant rate. The estradiol causes the animal to gain weight at a greater than normal rate. At the end of the growing period the implant can be readily removed from the animal to allow a withdrawal period prior to slaughter. It is an advantage of the present implant that it remains intact within the animal and can be easily and completely removed.

As will be explained below, the estradiol is dispersed throughout the coating of the implant. It diffuses through the coating to the surface of the implant where it is released into the animal tissue. There is an initial burst effect of a high concentration of estradiol released, but the release rate quickly levels out. The initial burst effect is believed to be due to a small amount of estradiol on the surface of the implant.

The biocompatible inert core material of the present implant may be any of a number of substances such as for example polyethylene, polypropylene, cellulose acetate, nylon, polymethylmethacrylate, silicone rubber, or even glass. The inert core should be non-toxic to the body and of a material which will not produce an adverse body reaction. Silicone rubber is the preferred core material.

The inert core of the implant is coated with silicone rubber containing estradiol. We have found the dimethylpolysiloxane silicone rubbers to be especially suitable for use in the drug-containing coating. These rubbers provide an optimum diffusion rate for estradiol to permit a substantially constant rate of administration.

In general, the dimethylpolysiloxanes are room temperature vulcanizable rubbers which are employed with a curing agent as will be discussed in more detail below. A number of suitable dimethylpolysiloxane rubbers are sold commercially as liquid elastomers which can be mixed with a curing agent to obtain the solid rubber. Among such commercially available rubbers are those sold by the Dow Corning Corporation identified as Silastic 382 and MDX-4-4210. Such rubbers consist of two components, a first component comprising liquid, uncured rubber and a second component comprising a curing agent. The two components are mixed and the mixture is allowed to cure, sometimes with heating. Another suitable type of dimethylpolysiloxane rubber is a high consistency medical grade elastomer such as that sold by Dow Corning Corporation under the designation MDF-0198. Silicone rubbers are discussed in U.S. Pat. No. 3,279,996, the disclosure of which is incorporated herein by reference.

The concentration of estradiol in the coating may vary within the range of from about 5% to about 40%. A preferred range is from about 15% to about 25%. A concentration of 20% of estradiol in the dimethylpolysiloxane has been found to be most preferred.

The number of days that an implant will continue to release the drug is controlled by the thickness of the coating. The amount of drug released each day is a function of the size of the implant and the concentration of drug in the coating. It is desired, of course, that an efficacious amount of the estradiol be released from the implant each day.

We have found that an effective amount of the estradiol is released from a cylindrical implant having a length of from about 0.5 to about 6 cm. Preferably the cylindrical implant is from about 2 to about 4 cm. in length and still more preferably from about 2.5 to about 3.5 cm. in length. The optimum length of such a cylindrical implant is about 3 cm.

The diameter of the inert core in such a cylindrical implant is within the range of from about 2 to about 10 mm. A preferred diameter of the inert core is from about 3 to about 5 mm. with the most preferred range being from about 3.5 to about 4.5 mm.

The thickness of the coating applied to the inert core may vary from about 0.2 to about 1 mm. and preferably from about 0.25 to about 0.5 mm. As noted earlier, the thickness of the coating determines the duration of payout of the drug. While it is preferred that the thickness of the coating be uniform, this is not critical.

For purposes of administration of estradiol to a growing beef animal we have found a suitable implant to be one of cylindrical shape having a length of about 3 cm. using an inert core having a diameter of from about 3.5 to about 4.5 mm. and a coating thickness of from about 0.25 to about 0.5 mm. The thicker coating gives a payout of about 400 days while the thinner coating gives a payout of about 200 days. In order to maintain the overall diameter of the implant the same regardless of the thickness of coating, the inert inner core diameter is varied with a more narrow core being used with a thicker coating. The preferred concentration of estradiol in the coating is 20%.

In preparing an implant of this invention the estradiol, preferably in a very fine particle size, is mixed mechanically with an uncured dimethylpolysiloxane rubber. A curing agent is then added to the mixture and this coating mixture is applied to the inert core. The coating is then cured at an appropriate temperature. The coating may be applied to the inert core in a mold to obtain any shape desired.

As mentioned above, we have found a cylindrical implant to be a preferred embodiment of this invention. To prepare such a cylindrical implant a continuous rod of the inert core material can be coated with the mixture of drug, uncured rubber and curing agent in a continuous process using a cross-head die of the type used in wire coating operations. After the coating has been cured at an appropriate temperature the continuous coated rod can be cut into appropriate lengths. Care must be exercised in the curing operation to be sure that the temperature used is not so high as to cause degradation of the estradiol.

The effectiveness of the implant of this invention as a system for the delivery of estradiol to a ruminant animal has been demonstrated by in vitro and in vivo tests. Such tests are described below.

Estradiol payout of the implants of this invention was measured in vitro by placing the implant in a sample vial with 25 ml. of 0.5% sodium lauryl sulfate in water. The vial was placed in a reciprocating shaker at 38° C. Samples of the sodium lauryl sulfate solution were removed periodically and the absorbance at 288 nm. was measured on a recording spectrophotometer and compared to the absorbance of standards prepared by dissolving known amounts of estradiol in 0.5% sodium lauryl sulfate.

Samples were analyzed daily for the first two weeks, weekly for the next four weeks, and every two weeks after that. The sodium lauryl sulfate solution was replaced with fresh solution each time a sample was taken for analysis. The average daily payout was determined by measuring the total estradiol in the 25 ml. of sodium lauryl sulfate solution and dividing by the number of days in the sampling period. Three replicates were used in each test.

In one such in vitro test two types of implants were studied. Both were cylindrical, 2.54 cm. long with a total diameter of 4.76 mm. The inert core was silicone rubber and the coating was 20% estradiol in Dow Corning MDX-4-4210. The ends of the core were not coated. One implant had a coating thickness of 0.25 mm. and the other had a coating thickness of 0.5 mm. The average daily payout in micrograms of estradiol per day is reported in the following table.

|      | Average Daily Payout, mcg. | |
| --- | --- | --- |
| Days | 0.5 mm. coating | 0.25 mm. coating |
| 7    | 282 | 291 |
| 14   | 212 | 260 |
| 28   | 146 | 155 |
| 56   | 103 | 89  |
| 112  | 63  | 66  |
| 168  | 52  | 51  |
| 224  | 36  | 42  |
| 280  | 34  | 34  |
| 336  | 33  | 29  |
| 392  | 29  | 29  |
| 448  | 30  | 28  |
| 504  | 28  | —   |

Three trials were conducted involving steers in the finishing phase of growth. Each treatment was replicated two or three times in each trial with five to fifteen steers in each replicate. The cylindrical implants comprised a silicone rubber inert core 4.26 mm. in diameter coated with Dow Corning MDX-4-4210 silicone rubber containing 20% estradiol. The core was not coated at each end. The thickness of the coating was 0.25 mm. giving an overall diameter of 4.76 mm. (3/16 inch). The implants varied in length from 0.635 cm. (¼ inch) to 3.81 cm. (1½ inches). The implants were placed subcutaneously in the posterior median surface of the ear. Control animals were implanted with placebo implants of untreated silicone rubber. Average initial weights of the animals ranged from 450 to 620 pounds over the three trials. The trials lasted from 146 to 208 days. All animals were fed a complete ration ad libitum. The animals were weighed at approximately 28 day intervals. The summary of the results of the three trials are given in the table below. The first column gives the length of the implant, the second column gives the average daily gain (ADG), the third column gives the average daily feed intake (ADF) and the fourth column gives the feed to gain ratio (F/G).

| Implant (cm.) | ADG (lbs.) | ADF (lbs.) | F/G |
| --- | --- | --- | --- |
| 2.54 (Control) | 2.30 | 18.8 | 8.21 |
| 0.635 | 2.56 | 20.7 | 8.06 |
| 1.27  | 2.64 | 20.6 | 7.77 |
| 2.54  | 2.68 | 20.4 | 7.58 |
| 3.81  | 2.67 | 20.4 | 7.63 |

The treated animals showed a statistically significant improvement over the control animals.

Growing-finishing steers were treated in nine trials. The implants used were the same as those described in the finishing trials except that the core diameter was 3.76 mm. and the coating thickness was 0.50 mm., giving a total diameter of 4.76 mm. The average initial weight of the animals in all nine trials was between 400 and 600 pounds. There were two replicates of each treatment with 8-10 steers per replicate. The pasture quality varied considerably over the nine trials, but all treatments and the controls were equally represented in each pasture. Duration of the pasture trials ranged from 100 to 191 days. The steers were weighed at approximately 28 day intervals. Upon completion of the pasture trials, animals from six of the trials were placed in feedlots and fed a complete ration ad libitum for 84 to 157 days. The animals were weighed at approximately 28 day intervals. The average daily gain of control and treated animals are summarized in the table below. The treated animals showed significantly improved gain over controls.

| Implant (cm.) | ADG (lbs.) | | |
|---|---|---|---|
| | Pasture (9 Trials) | Feedlot (6 Trials) | Both (6 Trials) |
| 2.54 (Control) | 1.16 | 2.65 | 1.98 |
| 0.635 | 1.21 | 2.89 | 2.13 |
| 1.27 | 1.25 | 2.73 | 2.08 |
| 2.54 | 1.26 | 2.91 | 2.18 |
| 3.81 | 1.22 | 2.95 | 2.18 |

Six trials were conducted on suckling calves. Five of those trials were carried on through a growing phase on pasture and four of the five growing trials were then carried on through a feedlot finishing phase. The implants used were the same as those previously described in the growing-finishing trial. The same implant was left in the animal through all three phases. Between 60 and 120 steer calves were used in each trial. Initial weights ranged from 135 to 285 pounds over the six trials. The animals were weighed at intervals of 25 to 56 days and at the beginning and end of each phase. During the suckling and growing phases all treatments and controls were equally represented in each pasture. The suckling phase averaged 148 days, the growing phase 186 days and the finishing phase 97 days. The average daily gain in each phase and for all three phases are summarized in the following table.

| Implant (cm.) | ADG (lbs.) | | | |
|---|---|---|---|---|
| | Suckling | Growing | Finishing | All Three |
| 2.54 (Control) | 1.92 | 1.12 | 2.92 | 1.86 |
| 0.635 | 2.02 | 1.12 | 2.86 | 1.87 |
| 1.27 | 1.99 | 1.12 | 2.99 | 1.91 |
| 2.54 | 2.02 | 1.22 | 3.08 | 1.98 |
| 3.81 | 2.00 | 1.21 | 3.05 | 1.96 |

It is a further advantage of this invention that the effective dose of estradiol is much less when administered by the claimed implant than when administered orally. We have found that the minimum dose of estradiol to give maximum benefit is 12 mcg./day and 39 mcg./day for suckling calves and feedlot cattle, respectively, when the present implant is used. Published results on the oral administration of estradiol report that the minimum dose for maximum response in feedlot cattle is 40,000 mcg./day.

It is believed that the low dose rate allows the amount of estradiol in the animal to return to the naturally-occurring base line level within a short time after the implant is removed from the body. We have found the amount of estradiol in the animal to return to the base line value within 24 hours after removing the implant. This permits a short drug withdrawal time.

We claim:
1. A solid, cylindrical, subcutaneous implant for improving the rate of weight gain of ruminant animals which comprises
    (a) a biocompatible inert core having a diameter of from about 2 to about 10 mm. and
    (b) a biocompatible coating having a thickness of from about 0.2 to about 1 mm., the composition of said coating comprising from about 5 to about 40 percent by weight of estradiol and from about 95 to about 60 percent by weight of a dimethylpolysiloxane rubber.
2. An implant of claim 1 wherein the biocompatible inert core is a silicone rubber.
3. An implant of claim 1 wherein the diameter of the inert core is from about 3.5 to about 4.5 mm., the thickness of the coating is from about 0.25 to about 0.5 mm., and the concentration of estradiol in the coating is from about 15 to about 25 percent.
4. An implant of claim 3 wherein the biocompatible inert core is a silicone rubber.
5. An implant of claim 4 wherein the concentration of estradiol in the coating is about 20 percent.
6. A method for the administration of estradiol to a ruminant animal which comprises placing an implant of claim 1 under the skin of the animal.
7. A method for the administration of estradiol to a ruminant animal which comprises placing an implant of claim 5 under the skin of the animal.

* * * * *